(12) United States Patent
Granger

(10) Patent No.: US 6,223,074 B1
(45) Date of Patent: Apr. 24, 2001

(54) METHOD AND COMPUTER PROGRAM PRODUCT FOR ASSESSING NEUROLOGICAL CONDITIONS AND TREATMENTS USING EVOKED RESPONSE POTENTIALS

(75) Inventor: Richard Granger, Irvine, CA (US)

(73) Assignee: Thuris Corporation, Irvine, CA (US)

( * ) Notice: Subject to any disclaimer, the term of this patent is extended or adjusted under 35 U.S.C. 154(b) by 0 days.

(21) Appl. No.: 09/407,368

(22) Filed: Sep. 28, 1999

Related U.S. Application Data

(63) Continuation-in-part of application No. 09/370,988, filed on Aug. 10, 1999, now abandoned.

(51) Int. Cl.⁷ .................................................. A61B 5/04
(52) U.S. Cl. ............................................ 600/544; 128/920
(58) Field of Search .................................... 600/544, 545, 600/546; 128/920, 923

(56) References Cited

U.S. PATENT DOCUMENTS

| | | |
|---|---|---|
| 4,214,591 | 7/1980 | Sato et al. . |
| 4,844,086 * | 7/1989 | Duffy .................................. 600/544 |
| 4,862,359 * | 8/1989 | Trivedi et al. ....................... 600/544 |
| 4,913,160 | 4/1990 | John . |
| 4,926,969 * | 5/1990 | Wright et al. ........................ 600/544 |
| 5,083,571 | 1/1992 | Prichep . |
| 5,230,346 * | 7/1993 | Leuchter et al. ..................... 600/544 |
| 5,287,859 | 2/1994 | John . |
| 5,357,976 | 10/1994 | Feng . |
| 5,769,074 | 6/1998 | Barnhill et al. . |
| 5,792,062 | 8/1998 | Poon et al. . |
| 5,816,247 | 10/1998 | Maynard . |
| 5,873,823 | 2/1999 | Eidelberg et al. . |
| 6,052,619 * | 4/2000 | John ..................................... 600/544 |

* cited by examiner

*Primary Examiner*—Samuel G. Gilbert
*Assistant Examiner*—Navin Natnithithadha
(74) *Attorney, Agent, or Firm*—Sterne, Kessler, Goldstein & Fox P.L.L.C.

(57) ABSTRACT

A method is provided for diagnosing the presence of a neurological disorder or otherwise assessing the neurological condition of a patient. The method also allows the assessment of a treatment regimen used by a patient. The method includes the collection and analysis of ERP data. The method of the invention begins by conducting a plurality of ERP trials on a patient. In an embodiment of the invention, the data from the ERP trials is then characterized to produce a single characterizing ERP signal vector for the patient. Projections based on the characterizing ERP signal vector are then generated. The projections are compared to information derived from the ERP data of patients having known neurological conditions. To perform diagnosis, the projections are compared to standards, such as one or more characterizing ERP signal vectors from known healthy patients, and one or more characterizing ERP signal vectors from s patient known to have the disorder. The probable presence or absence of the neurological disorder is decided by a weighted vote of the projections, where the weighting is a function of how closely each projection compares to the respective standards. Projections can also be used to perform other types of neurological assessment, such as tracking a patient's response to a treatment regimen, assessing the treatability of a patient with respect to a particular regimen, or determining the effects of a particular regimen.

55 Claims, 12 Drawing Sheets

METHOD AND COMPUTER PROGRAM PRODUCT FOR ASSESSING NEUROLOGICAL CONDITIONS AND TREATMENTS USING EVOKED RESPONSE POTENTIALS

The present application is a continuation-in-part of application Ser. No. 09/370,988, filed in the U.S. Patent and Trademark Office on Aug. 10, 1999, which was abandoned on Nov. 3, 1999.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The invention described herein relates to assessment of medical conditions, and more particularly to the assessment of neurological conditions through statistical methods.

2. Related Art

It is well known that neurological anomalies can be reflected in the electrical activity of the brain. Such electrical activity is therefore commonly used to diagnose a variety of neurological disorders or to evaluate the treatment thereof. Electrical activity in the brain is typically captured and analyzed in the form of an electroencephalograph (EEG).

Neurological diagnosis using EEGs has a number of drawbacks, however. An EEG, when viewed as a waveform, can only be analyzed with respect to frequency and power. An EEG cannot be analyzed in the time domain given that an EEG represents brain activity uncorrelated to any particular event in time. Moreover, EEGs tend to have significant variance over multiple trials even when performed on the same individual. This is due, in part, to the tendency of patients to react to ambient stimuli while the EEGs are being taken. In addition, EEGs, as signals, tend to have a low signal to noise ratio (SNR). Once collected, EEGs are difficult to analyze because of these factors. Analysis of EEGs by medical personnel tends to be difficult and time consuming.

Because of the difficulties in performing EEG analysis, the use of evoked response potentials (ERPs) has been proposed. An ERP represents neural electrical activity that occurs as a result of a specific sensory stimulus to the patient, such as a flash of light or a tone. The electrical activity, measured as voltage (that is, potential), is therefore an evoked response to a stimulus. Like an EEG, an ERP is typically collected and analyzed as a waveform. Unlike an EEG, however, an ERP can be analyzed in the time domain as well as the frequency domain. ERPs also tend to be less variable than EEGs over multiple trials on a given patient. Nonetheless, as in the case of EEGs, artifacts occur in ERPs and their removal is difficult and error-prone. Noise reduction is also difficult. The use of ERPs as a diagnostic tool is thus expensive and time consuming. Attempts to automate ERP processing have not been widely successful.

Hence there is a need for a method of assessing the neurological condition of a patient, where the method obtains and processes relatively consistent, low noise, artifact-free data. Moreover, the diagnostic method must be fast, inexpensive, and reliable.

SUMMARY OF THE INVENTION

The invention described herein provides a method of diagnosing the presence of a neurological disorder (such as Alzheimer's Disease, depression, or schizophrenia), otherwise assessing the neurological condition of a patient, or characterizing the results of a treatment regimen used by a patient. The method includes the collection and analysis of ERP data. The method of the invention begins by conducting a plurality of ERP trials on a patient. In an embodiment of the invention, the data from the ERP trials is then characterized to produce a single characterizing ERP signal vector for the patient. This reduces the artifacts and noise level in the data. Projections based on the characterizing ERP signal vector are then generated. The projections are compared to information derived from the ERP data of patients having known neurological conditions. To perform diagnosis, for example, the projections are compared to standards, such as one or more characterizing ERP signal vectors from known healthy patients, and one or more characterizing ERP signal vectors from patients known to have the disorder. The probable presence or absence of the neurological disorder is decided by a weighted vote of the projections, where the weighting is a function of how closely each projection compares to the respective standards. Projections can also be used to perform other types of neurological assessment, such as tracking a patient's response to a treatment regimen, assessing the treatability of a patient with respect to a particular regimen, or determining the effects of a particular regimen.

BRIEF DESCRIPTION OF THE FIGURES

The foregoing and other features and advantages of the invention will be apparent from the following, more particular description of a preferred embodiment of the invention, as illustrated in the accompanying drawings.

DETAILED DESCRIPTION OF THE PREFERRED EMBODIMENTS

A preferred embodiment of the present invention is now described with reference to the figures where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other devices and applications.

I. Overview

The invention provides a method of diagnosing a neurological disorder or otherwise assessing the neurological condition of a patient. The method begins with the collection of ERP signals from the patient under assessment, using multiple trials. In an embodiment of the invention, the ERP signals are combined over all trials performed on the patient and characterized. This forms a single characterizing ERP signal vector of the patient under assessment. A series of projections of the vector are then created by eliminating components of the vector. An assessment can then be made as to the neurological condition of the patient.

Diagnosis, for example, can be performed by comparing the projections to ERP signals collected from one or more known healthy patients, in an embodiment of the invention. In this embodiment, projections of the vector are also compared to ERP signals collected from one or more patients known to have the neurological disorder. A determination can then be made as to whether the patient under assessment is afflicted with the disorder, based on these comparisons. In other applications of the invention, a patient's projections can be used in tracking the patient's response to a treatment regimen, assessing the treatability of the patient with respect to a particular regimen, or determining the effects experienced by a patient as a result of a particular regimen. The invention can also be used to evaluate a specific treatment regimen, such as a new drug, by assessing the response of a patient to the treatment.

II. Method of Diagnosis

Figure 1:
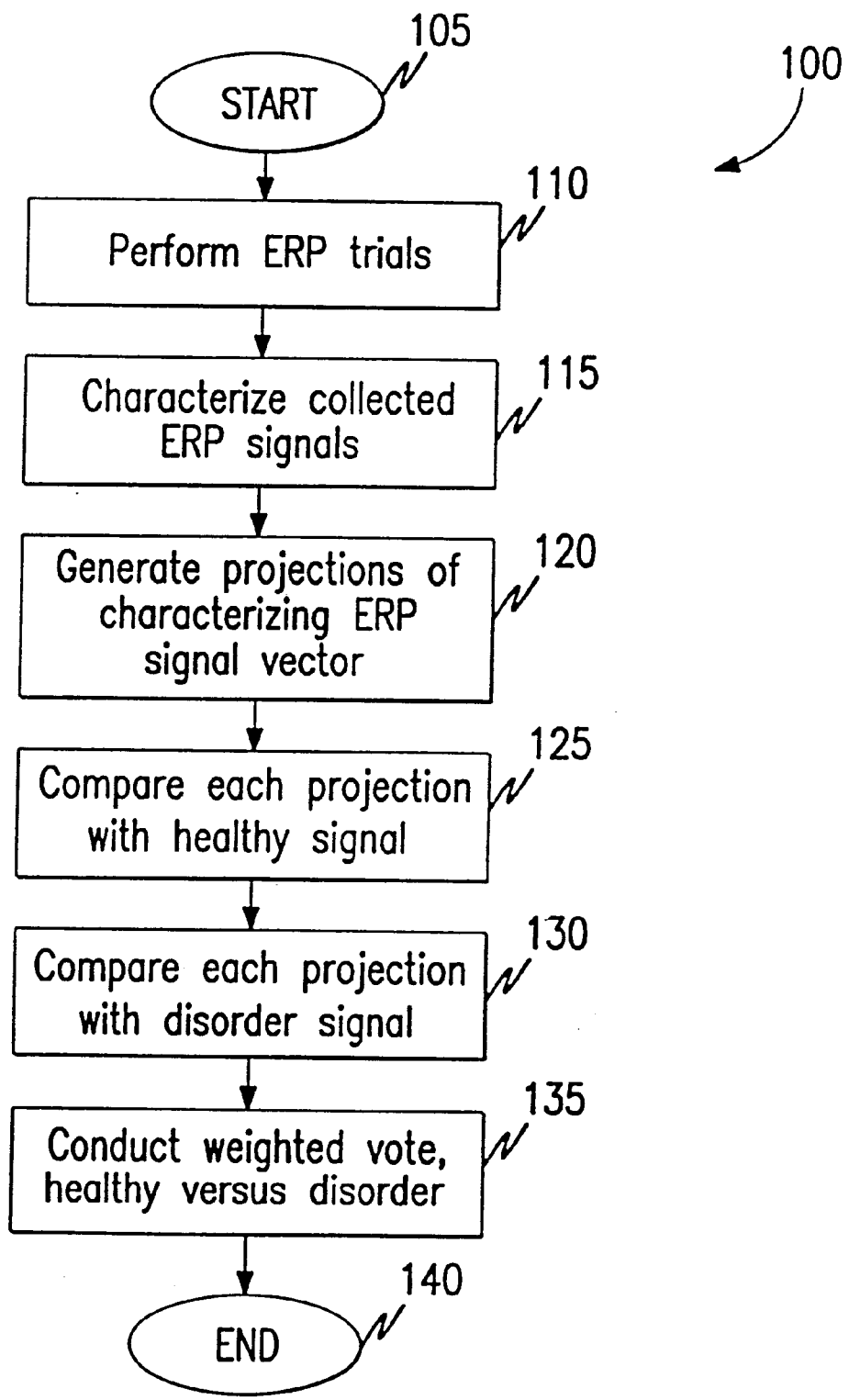
FIG. 1 is a flowchart illustrating the diagnosis process, according to an embodiment of the invention.

The method of the invention as used in diagnosis, according to one embodiment, is illustrated in flowchart 100 of FIG. 1. The process begins with a step 105. In a step 110, ERPs are elicited from a patient undergoing diagnosis. An ERP represents neural electrical activity that follows a sensory stimulus. Examples of such a stimulus are a flash of light or an auditory tone. A single stimulus and the electrical activity that follows constitute a trial. In an embodiment of the invention, a stimulus is presented every one to two seconds over an interval of approximately two minutes. The electrical activity is measured by a set of approximately 20 electrodes, each of which measures the voltage, or potential, about every ten milliseconds (msec). The result is a set of ERP signals, or waveforms, for each electrode, where each waveform represents a response to an instance of a stimulus. Each waveform is therefore approximately one to two seconds in length.

In a step 115, these ERP signals are combined and characterized to form a single characterizing ERP signal vector for the patient under assessment. Such a vector represents the patent's overall response to sensory stimuli. The characterization is performed in such a manner as to reduce extraneous artifacts and improve the SNR of the ERP data. In an embodiment described below, ERP signals are averaged over multiple trials. Other embodiments can use other forms of characterization, provided that the characterization operation considers all the ERP signals. Moreover, the characterizing ERP signal vector resulting from such a process must reflect the patient's tendencies with respect to the ERPs while minimizing noise and artifacts.

In a step 120, projections of the characterizing ERP signal vector are generated. A projection of a vector is produced when some of the coordinates of the vector are eliminated. In an embodiment of the invention, the coordinates that are eliminated are randomly chosen. In an alternative embodiment, the coordinates to be eliminated are chosen in a deterministic manner. In either case, the result is a group of projections, where each projection is a vector having fewer coordinates than the original characterizing ERP signal vector. If the characterizing ERP signal vector is viewed as a point in an information space, then this step serves to project the characterizing ERP signal vector into information subspaces of lower dimension.

Note that, in an alternative embodiment of the invention, projections are generated based on the ERP signals themselves rather than on a characterization of the ERP signals. In such an embodiment, the characterization step 115 is not necessary.

Once projections have been generated in step 120, a determination can be made as to whether the patient is likely to be afflicted with the neurological disorder. In an embodiment of the invention, this determination includes steps 125 through 135 of flowchart 100. In step 125, each projection is compared to one or more characterizing ERP signal vector of one or more healthy patients, respectively. In step 130, each projection is compared to one or more characterizing ERP signal vectors from one or more patients known to have the neurological disorder. For each projection, the goal is to determine, first, how closely the projection resembles the characterizing ERP signal vectors of one or more healthy patients, and second, how closely the projection resembles the characterizing ERP signal vector of one or more afflicted patients. In an embodiment of the invention, the comparisons are performed by calculating a statistical measure of resemblance (such as correlation) between each projection and the characterizing ERP signal vectors of the healthy and afflicted patients, respectively.

In step 135, a determination is made as to whether the characterizing ERP signal vector of the patient under assessment bears a closer resemblance to that of a healthy patient or that of a patient having the neurological disorder. The determination is made by a weighted vote of the projections. For each characterizing ERP signal vector of a healthy patient, the resemblance statistics (e.g., correlations) of all the projections with respect to the characterizing ERP signal vector of the healthy patient are summed to create a healthy sum. Likewise, for each characterizing ERP signal vector of an afflicted patient, the resemblance statistics of all the projections with respect to the characterizing ERP signal vector of the afflicted patient are summed to create a disorder sum. All healthy and disorder sums are compared to determine whether the patient under assessment more closely resembles one of the healthy patients or more closely resembles one of the afflicted patients. The result of this comparison can then be used in diagnosis, to determine whether the patient under assessment is likely suffering from the disorder. The process concludes with a step 140.

A. Characterization of ERP Signals

Figure 2:
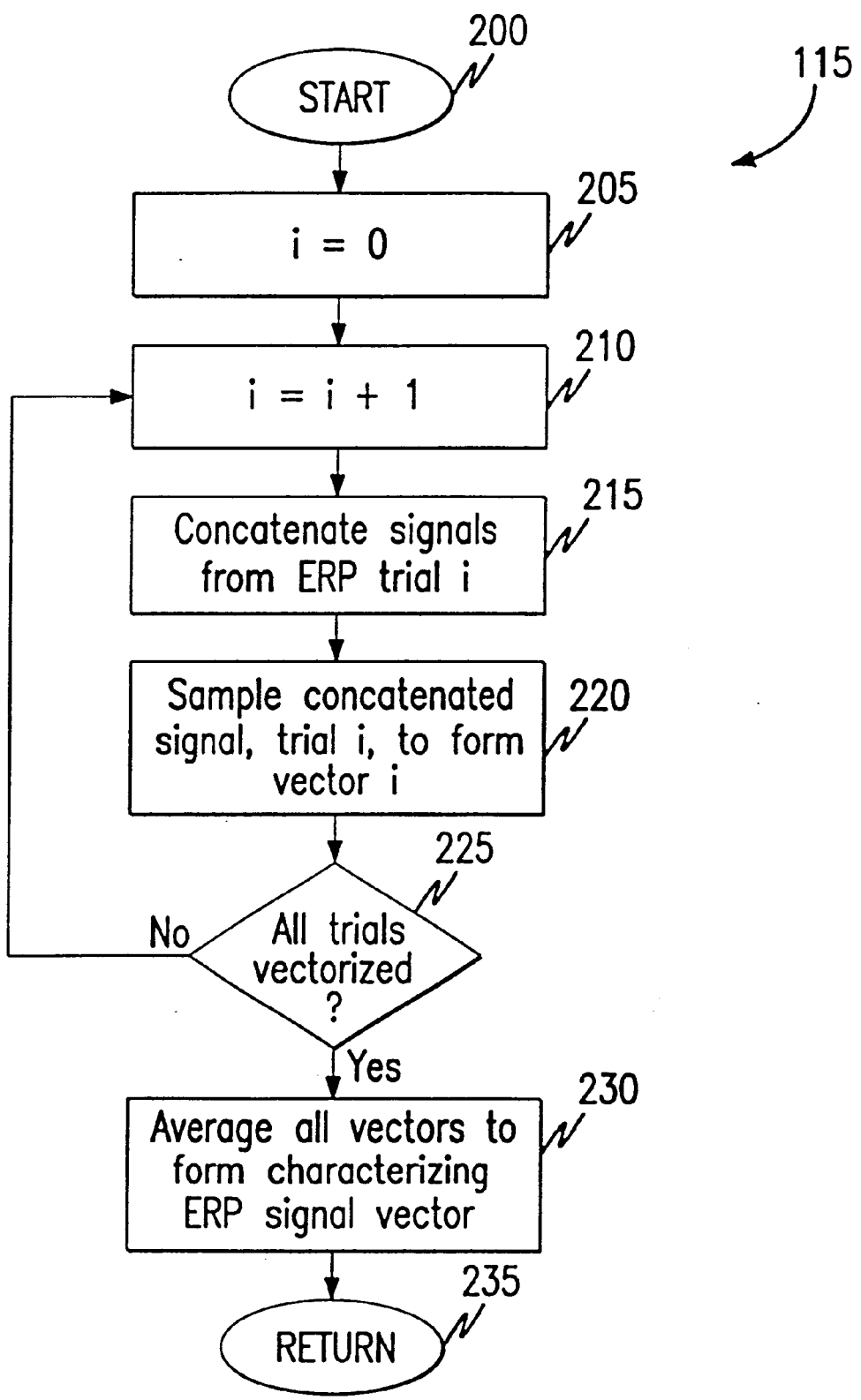
FIG. 2 is a flowchart illustrating the step of characterizing ERP data, according to an embodiment of the invention.

The characterization step 115 is illustrated in greater detail in FIG. 2. In the embodiment shown, the signals captured by each electrode for a given ERP trial are concatenated to form a single waveform. This waveform represents all the ERP data for the trial. The waveform is then sampled to produce a vector. The process is repeated for all trials. The resulting set of vectors includes one vector for each trial. The vectors are then averaged, by coordinate, to produce a characterizing ERP signal vector for the patient.

Figure 3:
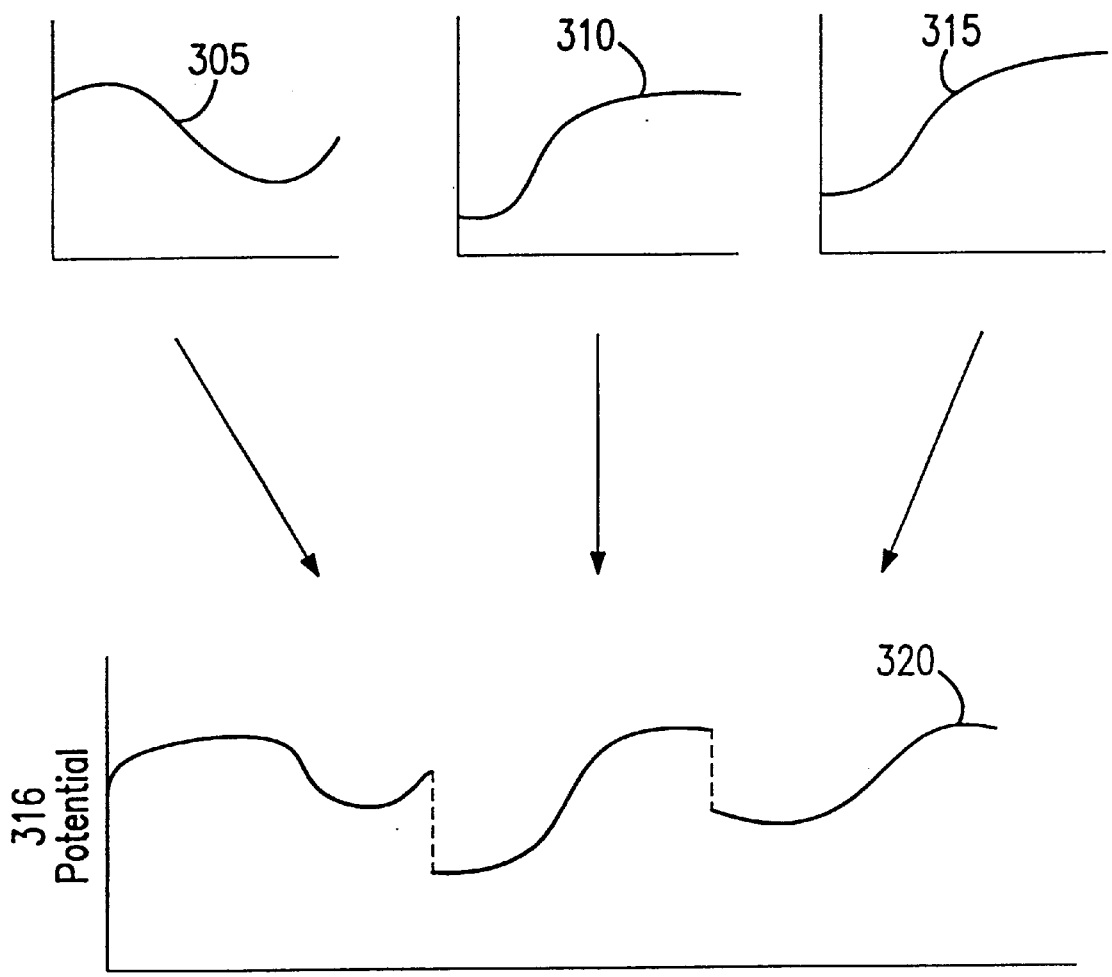
FIG. 3 illustrates the process of concatenating waveforms that represent ERP signals collected by different electrodes, according to an embodiment of the invention.

The process begins with a step 200. In steps 205 and 210, an index value i is initialized. Initially, i is set to 1, so that in a step 215, the signals collected by the electrodes during the first trial, trial 1, are concatenated to form a concatenated signal. Step 215 is illustrated graphically in FIG. 3, where signals 305, 310, and 315 are concatenated to form a concatenated signal 320.

Figure 4:
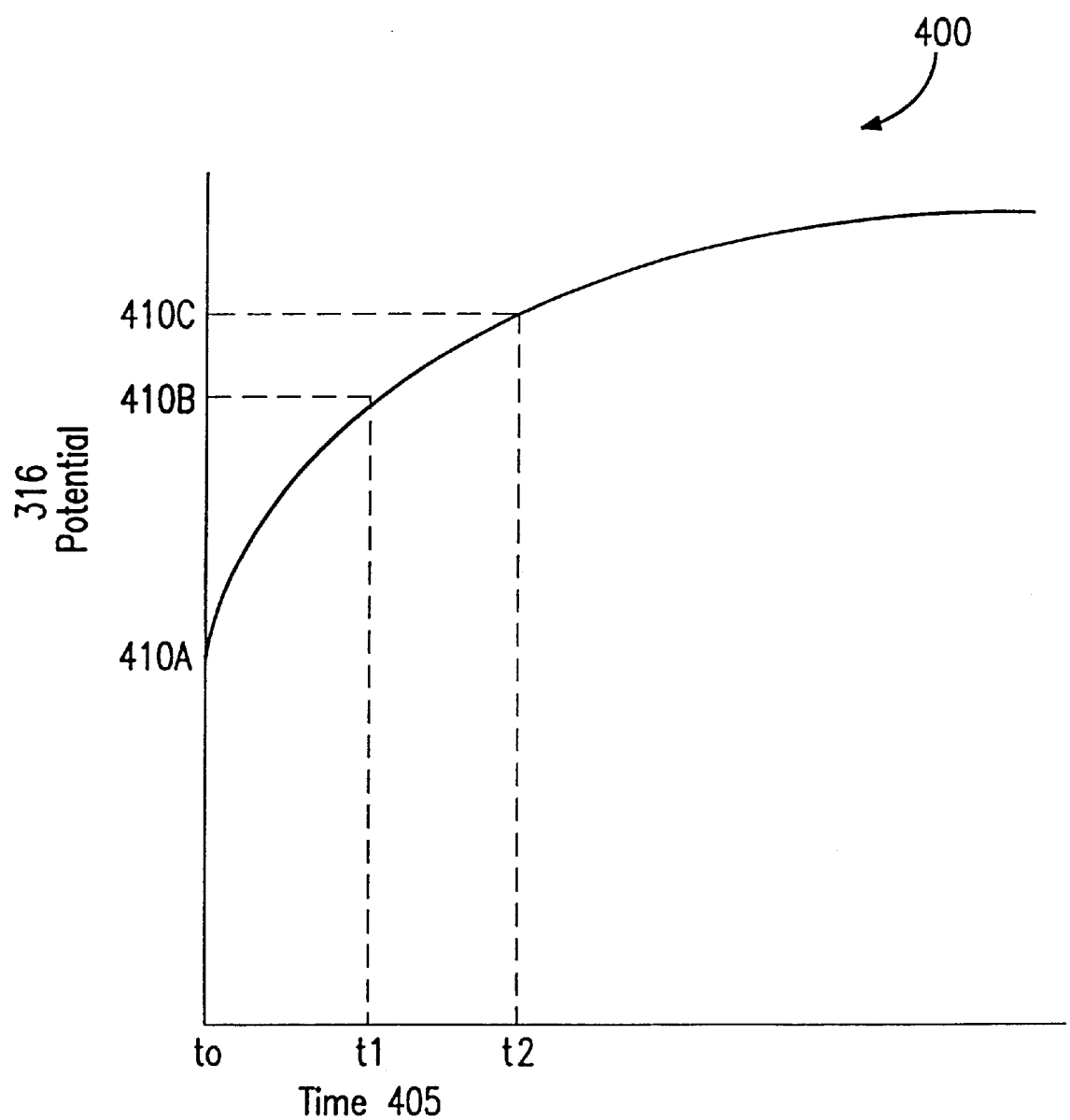
FIG. 4 illustrates the process of sampling a concatenated signal to produce a vector of amplitude values, according to an embodiment of the invention.

Returning to FIG. 2, in a step 220, the concatenated signal is sampled at a predetermined sampling rate to derive a vector of amplitude values. Sampling step 220 is illustrated graphically in FIG. 4. The amplitude, potential 316, of an example concatenated signal 400 is measured at fixed intervals, at points $t_0$, $t_1$, and $t_2$. The resulting set of amplitudes therefore includes the potentials corresponding to these points. These potentials are identified in FIG. 4 as potentials 410A, 410B, and 410C, respectively. In an embodiment of the invention, sampling is performed at intervals of approximately 10 msec.

Returning to FIG. 2, the set of amplitudes sampled in step 220 are saved in a single vector, vector 1, corresponding to trial 1. In a step 225, a determination is made as to whether the concatenated signal of the final trial has been converted into a vector. If not, the process returns to step 210, where the index i is incremented so that the ERP signals from the next trial can be processed. The ERP signals from the next trial are then concatenated, sampled, and converted into a vector. The process continues until the ERP signals from each trial have been converted into a vector, one vector per trial. The determination as to whether the ERP signals of the final trial have been converted into a vector is made in step 225. In a step 230, the vectors are averaged to form a characterizing ERP signal vector. This is performed on a per component basis. The nth component in the characterizing ERP signal vector is therefore the arithmetic mean of the nth components of all the individual vectors. Because the characterizing ERP signal vector is a function of all the ERP signals collected from the patient being diagnosed, noise and artifacts tend to be minimized. The characterization process 115 concludes with a step 235.

B. Comparison of a Characterizing ERP Signal Vector to Known Standards

Figure 5A:
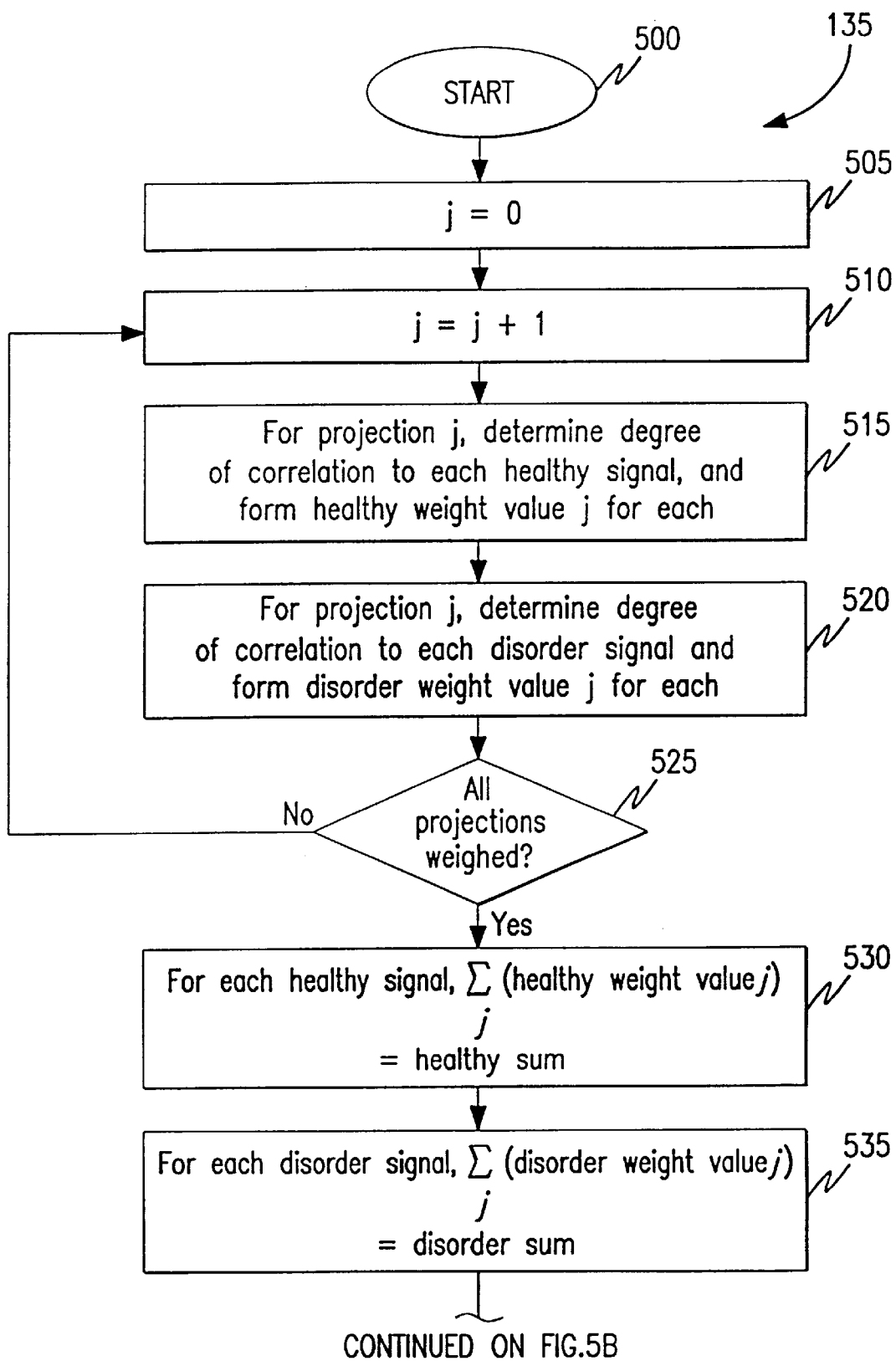
FIG. 5 is a flowchart illustrating the step of conducting a weighted vote to facilitate a diagnosis, according to an embodiment of the invention.
Figure 5B:
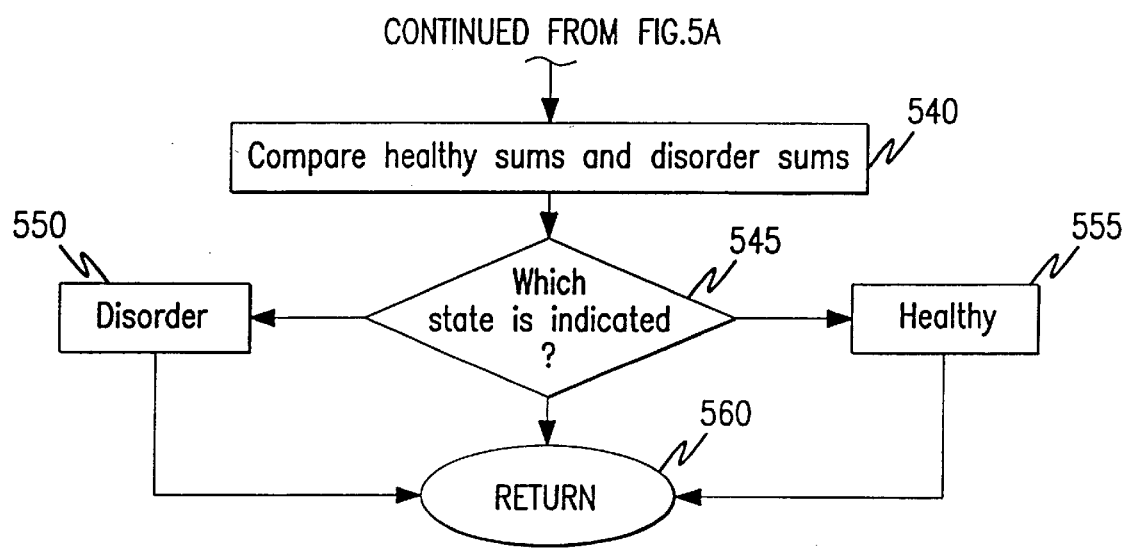

The comparison step 135 is illustrated in greater detail in FIG. 5. In the embodiment illustrated, each projection is compared to one or more characterizing ERP signal vectors of one or more healthy patients, respectively. Each projection is also compared to one or more characterizing ERP signal vectors of one or more afflicted patients, respectively. The corresponding correlations are then derived for each projection. The correlations are used to perform a weighted vote to decide whether or not the patient is more likely to be afflicted with the disorder.

Comparison step 135 begins with a step 500. In steps 505 and 510, an index j is initialized. Index j is used to keep track of the processing of the projections. In a step 515, the first projection, projection 1, is correlated to each of one or more characterizing ERP signal vectors taken from one or more healthy patients, respectively. These characterizing ERP signal vectors are known hereinafter as healthy signals. This results in a correlation statistic, referred to as a healthy weight value 1, for each healthy signal. In a step 520, projection 1 is correlated to one or more characterizing ERP signal vectors of one or more patients, respectively, where these patients are suffering from the neurological disorder. These vectors are known hereinafter as disorder signals. This results in a correlation statistic, referred to as a disorder weight value 1, for each disorder signal is. In a step 525, a determination is made as to whether all the projections have been correlated and their weight values calculated. If not, the process returns to step 510, where the index j is incremented. The correlation process is then performed with respect to the next projection.

If, in step 525, it is determined that all correlations have been performed on all the projections and the weight values determined, then the process continues with a step 530. In step 530, for each healthy signal, the healthy weight values are summed over all the projections. This produces a healthy sum for each healthy signal. In a step 535, for each disorder signal, the disorder weight values are summed over all the projections. This produces a disorder sum for each disorder signal. In a step 540, the healthy sums and the disorder sums are compared. Depending on which state is indicated in a step 545, the patient will be identified as more likely to have the disorder (a step 550) or more likely to be healthy (a step 555). The determination of step 545 is made by analyzing the healthy sums and disorder sums. If the largest sum is a healthy sum, for example, the patient under assessment may be more likely to be healthy. If the highest sum is a disorder sum, on the other hand, the patient under assessment may be more likely to be afflicted with the disorder. The process concludes with a step 560.

III. Other Applications

The techniques described above can address a range of problems broader than the diagnosis of neurological disorders. Examples of such problems, and the embodiments of the invention applicable to these problems, are discussed below.

A. Assessment of Treatability

An embodiment of the invention can be used to determine whether a patient having a neurological disorder is treatable using a particular treatment regimen. Such a regimen can consist of a particular dosage of a certain drug, such as PROZAC in the case of a patient suffering from depression. In this embodiment of the invention, projections of a patient's ERP data are created. The projections are then compared to one or more characterizing ERP signal vectors of one or more patients, respectively, known to be treatable by the particular treatment regimen. If the comparison reveals some degree of similarity between the condition of the patient under assessment and the condition of the patient (s) known to be treatable under the regimen, the treatability of the patient under assessment is suggested.

Figure 6:
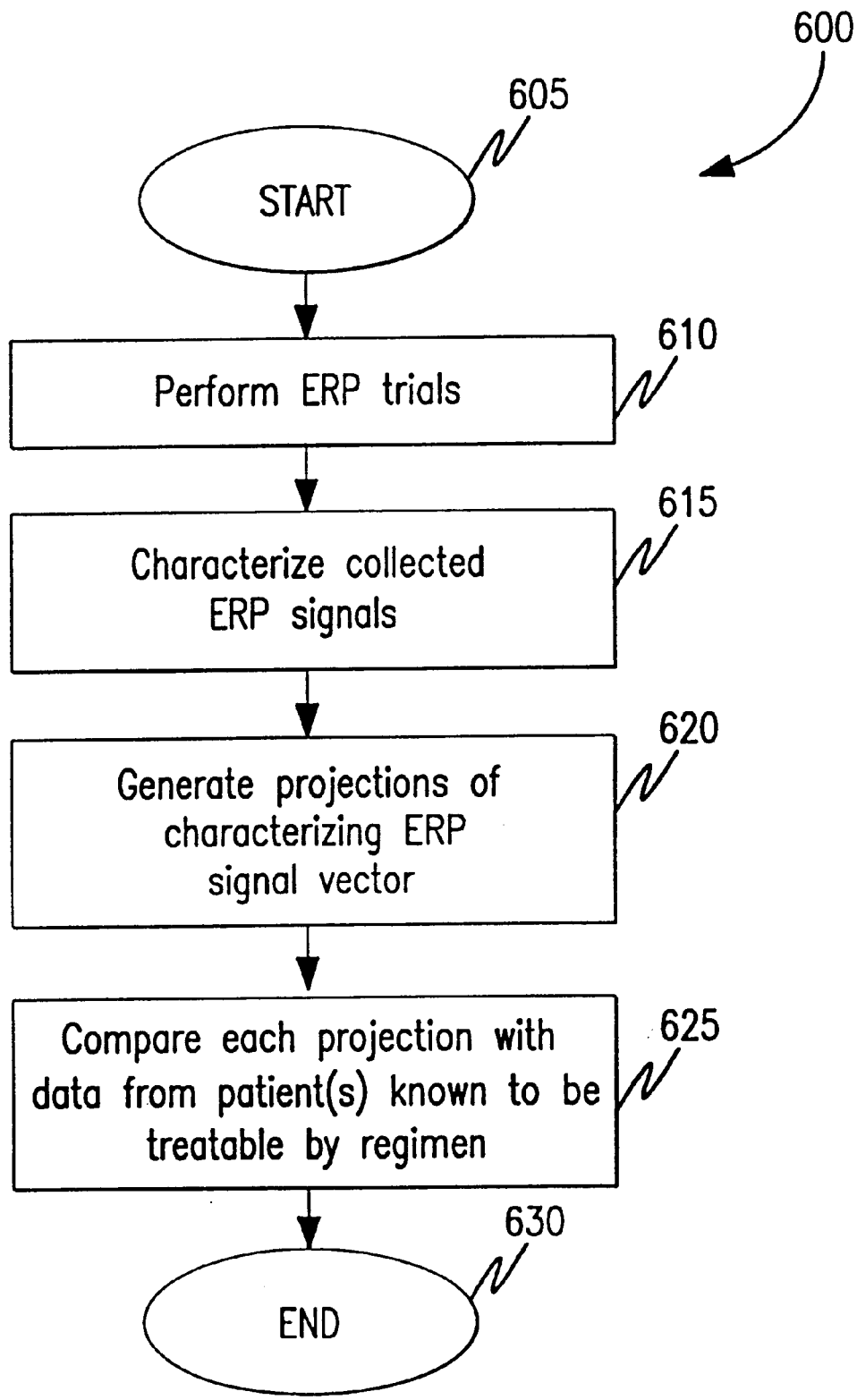
FIG. 6 is a flowchart illustrating the process for assessing the treatability of a patient, according to an embodiment of the invention.

An embodiment of the invention for the assessment of treatability of a patient is illustrated in FIG. 6. The process begins with a step 605. In steps 610 through 620, ERP data is collected, characterized, and processed to produce projections. These steps are analogous to steps 110 through 120 of FIG. 1. A determination is then made as to whether the patient is likely to be treatable given a particular treatment regimen. In the embodiment illustrated, this is done in a step 625 by comparing the projections to information derived from ERP data of one or more patients known to be treatable by the regimen. The projections can, for example, be compared to characterizing ERP signal vectors of the patients known to be treatable by the regimen. For each projection and characterizing ERP signal vector, a degree of correlation between the two is determined and assigned a first weight value. For each patient known to be treatable by the regimen, the first weight values over all projections are summed. For a given patient known to be treatable by the regimen, this yields a sum indicative of the treatability, with respect to the particular regimen, of the patient under assessment, relative to the given patient.

Note that this process can also be used to select a particular treatment from among a set of options. The process can be repeated, for example, in relation to a second treatment regimen. This would result in a weight value, known herein as a second weight value, for each projection and each of one or more patients known to be treatable with the second regimen. For a given patient known to be treatable by the second regimen, summing the second weight values over all projections yields a second sum. This latter sum would be indicative of the treatability of the patient under assessment, with respect to the second regimen, relative to the given patient. First sums and second sums can then be compared to evaluate the relative treatability of the patient with respect to the first and second treatment regimens. If, for example, the projections are more similar to patients treatable by one regimen than to patients treatable by the second, then this suggests that the first treatment regimen should be chosen. By analogy, this method can be extended to a plurality of treatment regimens, so that the relative treatablilty of the patient can be assessed with respect to this plurality of regimens.

B. Assessment of Progress During Treatment

An embodiment of the invention can also be used to assess the progress of a patient undergoing treatment for a neurological disorder. In this embodiment, projections of a patient's ERP data are created. The projections are compared to one or more characterizing ERP signal vectors of one or more other patients, respectively, where the other patients each have some known neurological condition. If the comparison reveals some degree of similarity between the condition of the patient under assessment and the condition of the other patient(s), then conclusions can be drawn as to the condition of the patient under assessment. If, for example, there is similarity between the condition of the patient under assessment and the condition of a patient who is neurologically healthy, this might suggest improvement in the condition of the patient under assessment. On the other hand, another patient may be afflicted with the same disorder for which the patient under assessment is being treated. Here, similarity between the condition of the patient under assessment and the condition of the afflicted patient might suggest a lack of improvement in the condition of the patient under assessment. Alternatively, another patient may have some other condition, one that represents a potential side effect of the treatment being used on the patient under assessment. Here, similarity between the condition of the patient under assessment and the condition of the patient suffering from the side effect might suggest the presence of the side effect in the patient under assessment.

Figure 7:
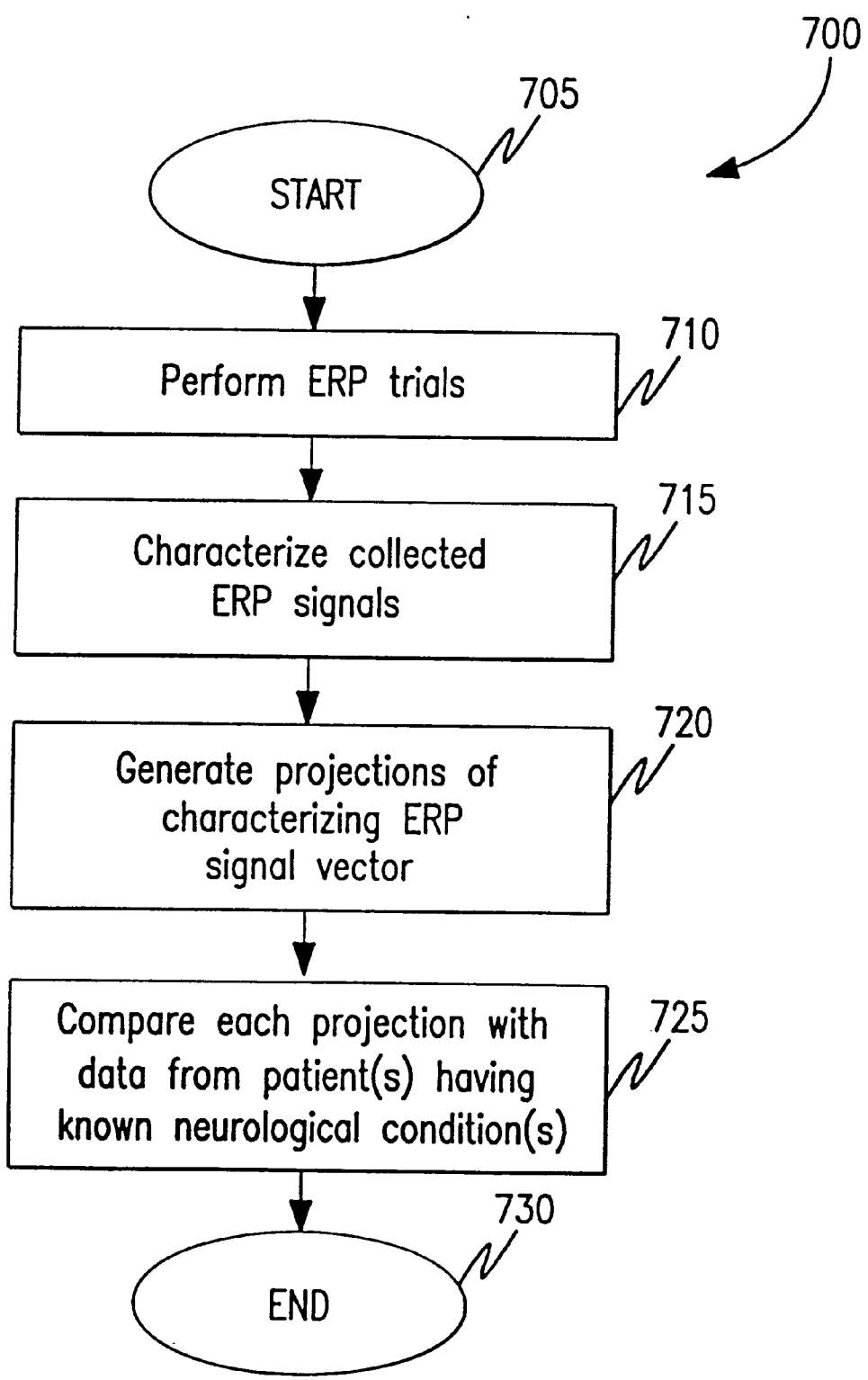
FIG. 7 is a flowchart illustrating the process for assessing the response of a patient to a treatment regimen, according to an embodiment of the invention.

An embodiment of the invention, as applied to assessment of a patient's progress under treatment, is illustrated in FIG. 7. The process begins with a step 705. In steps 710 through 720, ERP data is collected, characterized, and processed to produce projections. These steps are analogous to steps 110 through 120 of FIG. 1. A determination can then be made as to the progress of the patient under assessment. In the illustrated embodiment, this is done in a step 725. Here, each projection is compared with information derived from one or more other patients. In an embodiment of the invention, each projection is compared with one or more characterizing ERP signal vectors from one or more other patients, respectively. For each of the characterizing ERP signal vectors of the other patients, the degree of correlation between the characterizing ERP signal vector and each projection is determined. Each correlation is assigned a progress weight value.

Adding together the progress weight values over all projections with respect to the characterizing ERP signal vector of a given patient yields a progress sum that can be indicative of the condition of the patient under assessment, relative to the condition of the given patient. The summation process can be repeated with respect to the other patients as well. This yields a progress sum with respect to each of the other patients. As described above, the progress sums can facilitate inferences as to the progress of the patient under assessment.

C. Discerning Side Effects of Treatment

An embodiment of the invention can also be used to assess whether a patient undergoing treatment for a neurological disorder is experiencing side effects. This embodiment also allows assessment of the nature and extent of the side effects. In this embodiment, projections of a patient's ERP data are created and compared to characterizing ERP signal vectors of one or more other patients, where these patients each have a known neurological condition, e.g., a condition that represents a possible side effect of the treatment. The degree of similarity (or dissimilarity) between the projections and the characterizing ERP signal vectors of these other patients provides information suggesting the nature and degree of these side effects in the patient under assessment.

Figure 8:
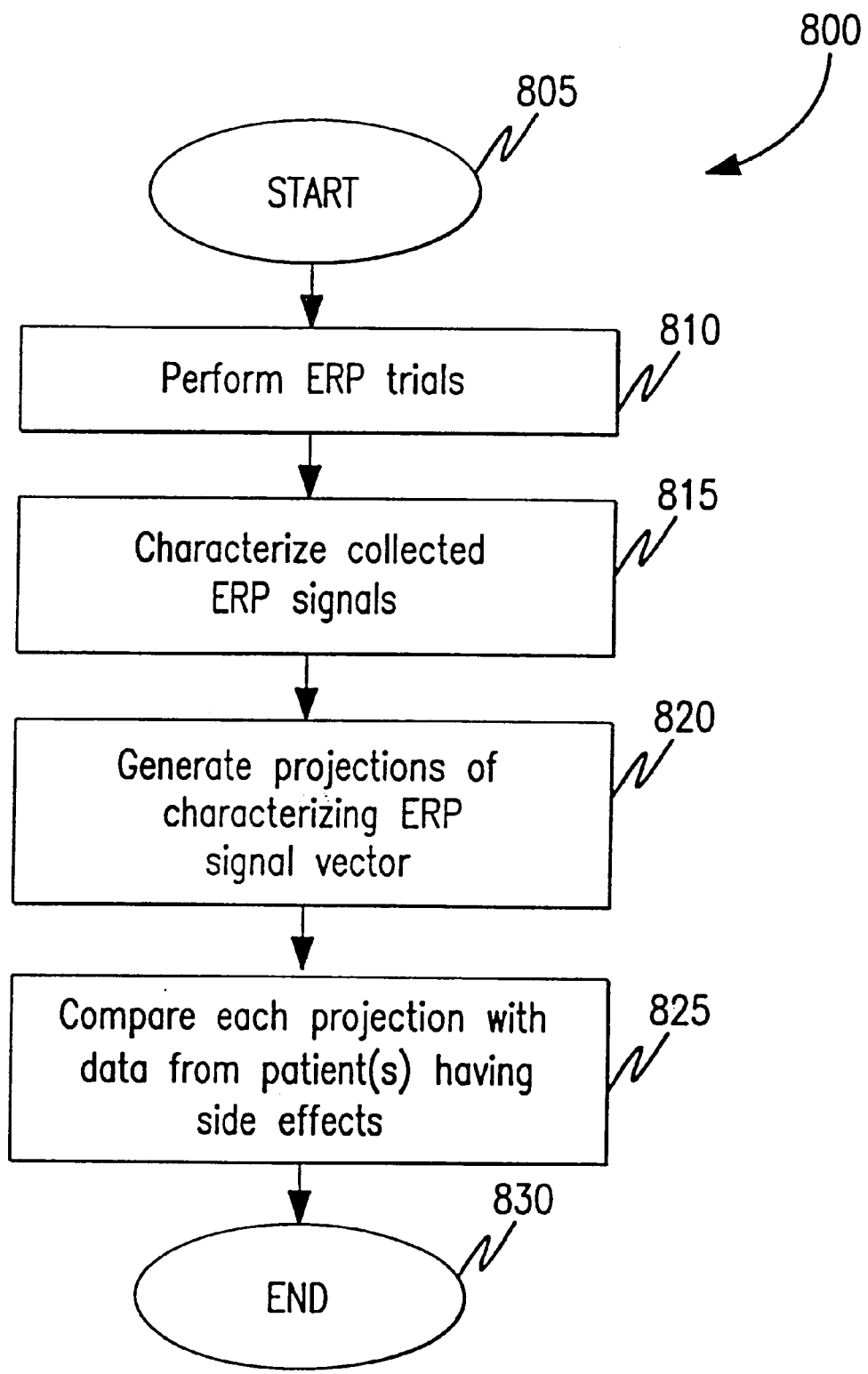
FIG. 8 is a flowchart illustrating the process for assessing the nature and extent of side effects resulting from a treatment regimen, according to an embodiment of the invention.

An embodiment of the invention, as applied to assessment of side effects experienced by a patient, is illustrated in FIG. 8. The process begins with a step 805. In steps 810 through 820, ERP data is collected, characterized, and processed to produce projections. These steps are analogous to steps 110 through 120 of FIG. 1. A determination is then made as to whether (and to what extent) the patient is likely suffering from any of a variety of side effects of a particular treatment regimen. In the embodiment illustrated, this is done in a step 825 by comparing the projections to information derived from the ERP data of one or more other patients. At the time the ERP data was collected from these other patients, these patients were known to have certain neurological conditions. For example, they may have been experiencing side effects from the treatment regimen in question. In one embodiment, the projections are compared to characterizing ERP signal vectors of the other patients. For each projection and each characterizing ERP signal vector of another patient, a degree of correlation between the projection and the characterizing ERP signal vector of the other patient is determined and assigned a side effect weight value. For each of the other patients, the side effect weight values over all projections with respect to the characterizing ERP signal vector of the other patient are added together. This yields a set of side effect sums, where each sum is indicative of the similarity of the condition of the patient under assessment to the side effect associated with one of the other patients. This allows evaluation of whether the patient under assessment is likely experiencing a particular side effect or combination of side effects, and the extent to which any given side effect is being experienced.

D. Evaluation of a Novel Treatment

While the invention can facilitate the assessment of a patient, the invention may also be used in the assessment of treatments themselves. By observing the response of a patient to a novel treatment, observations can be made about the treatment. If, for example, it is suspected that a given drug causes or tends to cause a certain side effect, this suspicion can be confirmed or refuted by using this process to assess a group of test patients. In addition, this process can be used to establish the likelihood that patients will experience a certain side effect, again, by using this invention to assess a group of test patients. This process also permits the discovery of new side effects if, for example, a test patient's projections fail to correlate to ERP data associated with known side effects.

In this embodiment of the invention, projections of a test patient's ERP data are created and compared to characterizing ERP signal vectors of one or more other patients, where these patients each have a known neurological condition. The degree of similarity (or dissimilarity) between the projections and the characterizing ERP signal vectors of these other patients provides information suggesting the effect of the treatment on the test patient.

Figure 9:
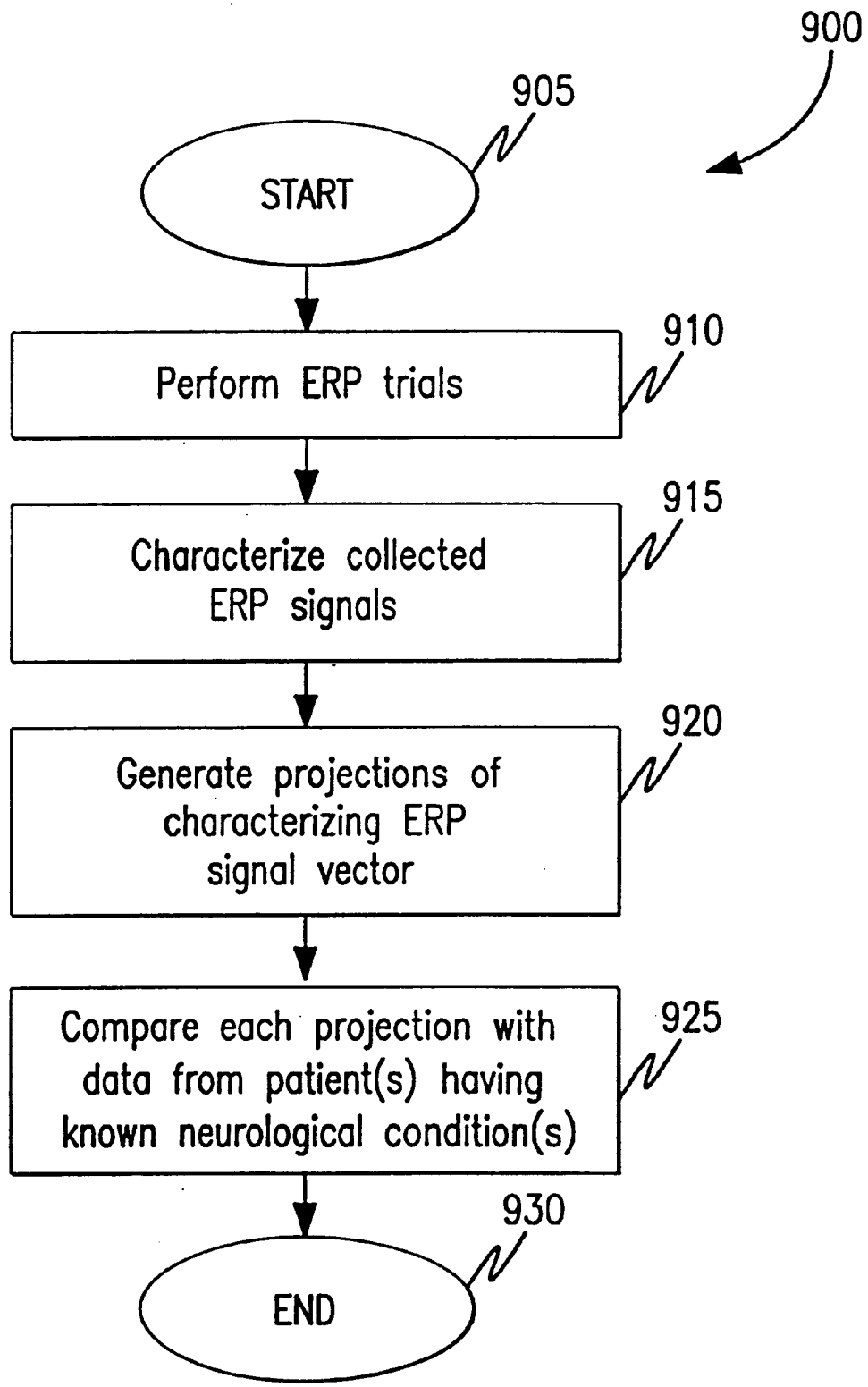
FIG. 9 is a flowchart illustrating the process for characterizing the results of a treatment regimen.

An embodiment of the invention, as applied to assessment of the results of a treatment regimen, is illustrated in FIG. 9. The process begins with a step 905. In steps 910 through 920, ERP data is collected, characterized, and processed to produce projections. These steps are analogous to steps 110 through 120 of FIG. 1. A determination is then made as to the test patient's likely neurological condition as a result of the treatment regimen. In the embodiment illustrated, this is done in a step 925 by comparing the projections to information derived from the ERP data of one or more other patients. At the time the ERP data was collected from these other patients, they were known to have certain neurological conditions. For example, some may have been experiencing some form of neurological disorder, or some may have been neurologically healthy. In one embodiment, the projections are compared to characterizing ERP signal vectors of the other patients. For each projection and each characterizing ERP signal vector of another patient, a degree of correlation between the projection and the characterizing ERP signal vector of the other patient is determined and assigned a comparison weight value.

For each of the other patients, the comparison weight values over all projections with respect to the characterizing ERP signal vector of the other patient are added together. This yields a set of comparison sums, where each comparison sum is indicative of the similarity of the condition of the test patient to the condition of one of the other patients. This allows assessment of the neurological condition of the test patient resulting from the treatment regimen and therefore allows characterization of the treatment's effects.

E. Generalized Application

Figure 10:
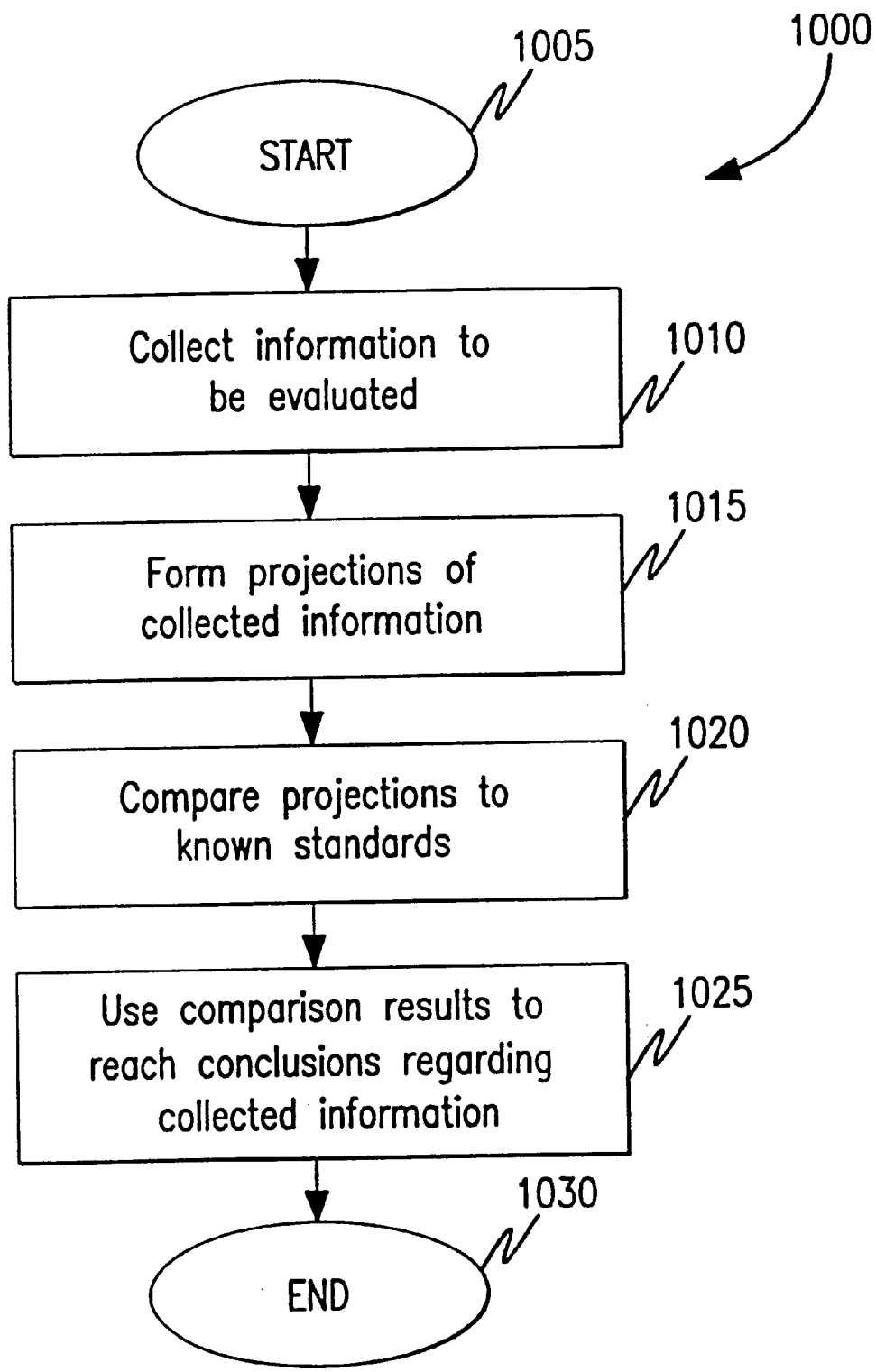
FIG. 10 is a flowchart illustrating a generalized method of an embodiment of the invention.

When generalized, the invention allows the processing of a body of information so as to permit conclusions about whether the information can be associated with a particular category or condition. Such an approach can be used, for example, in imaging or signal processing, where an image or signal must be identified or categorized. A general process for this is illustrated in FIG. 10. The process 1000 begins with a step 1005. In a step 1010, the information to be evaluated is collected. In a step 1015, projections of the collected information are created. Projections are formed, in general, by characterizing the collected information and eliminating portions of the characterization. This step projects the characterized information into information subspaces. The projections can then be compared to known standards in a step 1020, where the standards are representative of categories or conditions with which the information may be associated. In a step 1025, the results of the comparisons are used to reach conclusions about whether the collected information can be associated with one of the categories or conditions represented by the standards of step 1020. The process concludes with a step 1030.

IV. Environment

Figure 11:
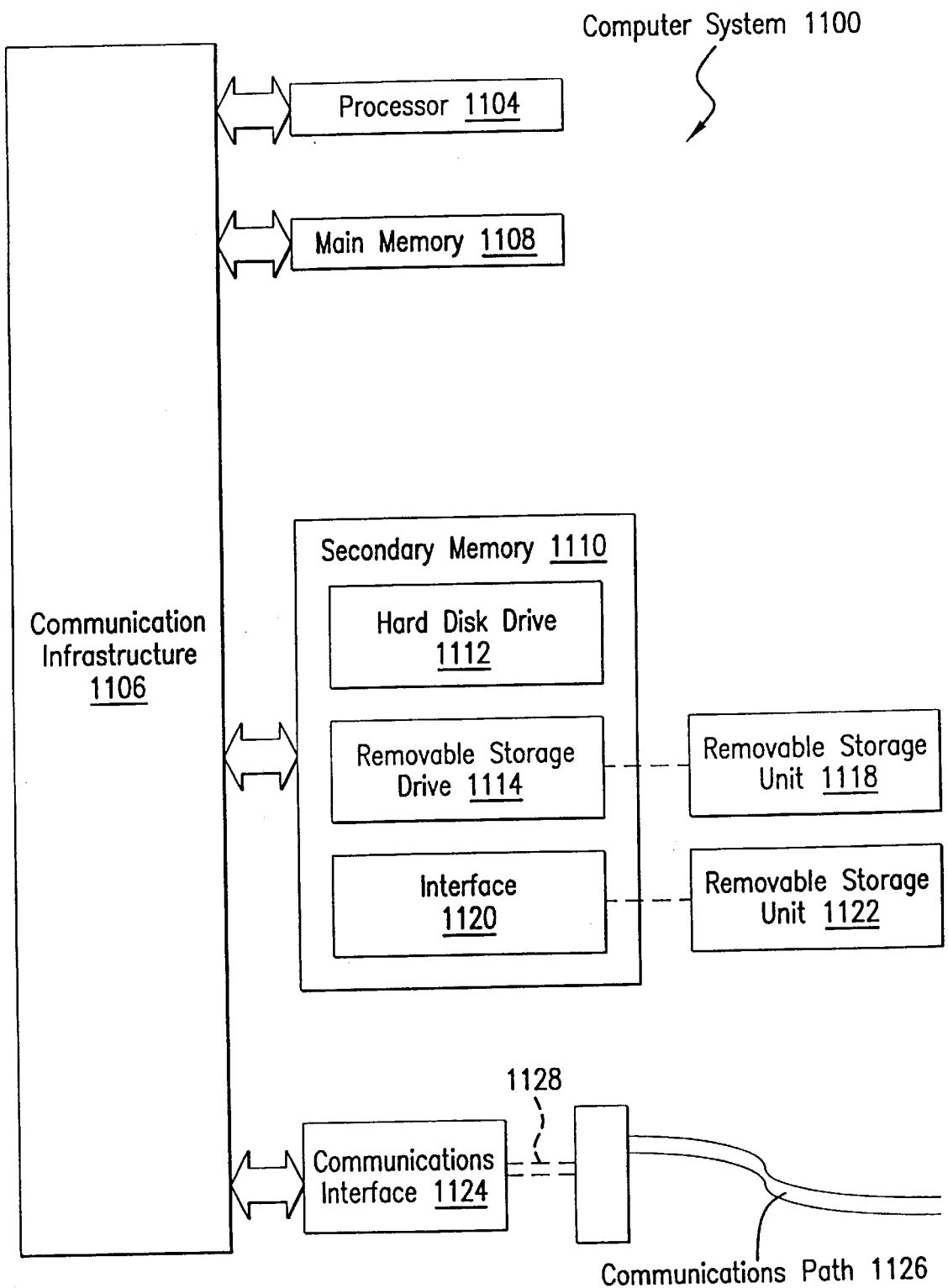
FIG. 11 illustrates an exemplary computer system that executes a software embodiment of the invention.

The present invention may be implemented using hardware, software or a combination thereof and may be implemented in a computer system or other processing system. An example of such a computer system 1100 is shown in FIG. 11. The computer system 1000 includes one or more processors, such as processor 1004. The processor 1104 is connected to a communication infrastructure 1106, such as a bus or network). Various software implementations are described in terms of this exemplary computer system. After reading this description, it will become apparent to a person skilled in the relevant art how to implement the invention using other computer systems and/or computer architectures.

Computer system 1100 also includes a main memory 1108, preferably random access memory (RAM), and may also include a secondary memory 1110. The secondary memory 1110 may include, for example, a hard disk drive 1112 and/or a removable storage drive 1114, representing a floppy disk drive, a magnetic tape drive, an optical disk drive, etc. The removable storage drive 1114 reads from and/or writes to a removable storage unit 1118 in a well known manner. Removable storage unit 1118, represents a floppy disk, magnetic tape, optical disk, or other storage medium which is read by and written to by removable storage drive 1114. As will be appreciated, the removable storage unit 1118 includes a computer usable storage medium having stored therein computer software and/or data.

In alternative implementations, secondary memory 1110 may include other means for allowing computer programs or other instructions to be loaded into computer system 1100. Such means may include, for example, a removable storage unit 1122 and an interface 1120. Examples of such means may include a program cartridge and cartridge interface (such as that found in video game devices), a removable memory chip (such as an EPROM, or PROM) and associated socket, and other removable storage units 1122 and interfaces 1120 which allow software and data to be transferred from the removable storage unit 1122 to computer system 1100.

Computer system 1100 may also include a communications interface 1124. Communications interface 1124 allows software and data to be transferred between computer system 1100 and external devices. Examples of communications interface 1124 may include a modem, a network interface (such as an Ethernet card), a communications port, a PCMCIA slot and card, etc. Software and data transferred via communications interface 1124 are in the form of signals 1128 which may be electronic, electromagnetic, optical or other signals capable of being received by communications interface 1124. These signals 1128 are provided to communications interface 1124 via a communications path (i.e., channel) 1126. This channel 1126 carries signals 1128 and may be implemented using wire or cable, fiber optics, a phone line, a cellular phone link, an RF link and other communications channels. In an embodiment of the invention, signals 1128 comprise ERP signals collected from a patient and characterizing ERP signal vectors from known healthy and afflicted patients. Alternatively, this information can be provided to computer system 1100 from secondary memory 1110.

In this document, the terms "computer program medium" and "computer usable medium" are used to generally refer to media such as removable storage units 1118 and 1122, a hard disk installed in hard disk drive 1112, and signals 1128. These computer program products are means for providing software to computer system 1100.

Computer programs (also called computer control logic) are stored in main memory 1108 and/or secondary memory 1110. Computer programs may also be received via communications interface 1124. Such computer programs, when executed, enable the computer system 1100 to implement the present invention as discussed herein. In particular, the computer programs, when executed, enable the processor 1104 to implement the present invention. Accordingly, such computer programs represent controllers of the computer system 1100. Where the invention is implemented using software, the software may be stored in a computer program product and loaded into computer system 1100 using removable storage drive 1114, hard drive 1112 or communications interface 1124. In an embodiment of the present invention, steps 115 through 135 of flowchart 100 can be implemented in software and can therefore be made available to processor 1104 through any of these means. Analogously, steps 615 through 625 of flow chart 600, steps 715 through 725 of flow chart 700, steps 815 through 825, and steps 915 through 925 of flow chart 900 can be implemented in software and can therefore be made available to processor 1104 through any of these means.

V. Conclusion

While various embodiments of the present invention have been described above, it should be understood that they have been presented by way of example, and not limitation. It will be apparent to persons skilled in the relevant art that various changes in detail can be made therein without departing from the spirit and scope of the invention. Thus the present invention should not be limited by any of the above-described exemplary embodiments, but should be defined only in accordance with the following claims and their equivalents.

What is claimed is:

1. A method of diagnosing a neurological disorder, comprising the steps of:
   (a) performing a plurality of evoked response potential (ERP) trials on a patient under assessment;
   (b) generating a plurality of projections of ERP data, wherein the ERP data is derived from the plurality of ERP trials performed on the patient under assessment; and
   (c) determining the presence of the neurological disorder by a weighted vote process that is based on the projections.

2. The method of claim 1, wherein said step (a) comprises the step of repeating an ERP trial approximately once every one to two seconds, for approximately two minutes.

3. The method of claim 1, further comprising the step of:
   (d) characterizing ERP signals obtained from the plurality of trials performed on the patient under assessment, to produce a characterizing ERP signal vector for the patient under assessment;
wherein said step (d) is performed after said step (a) and before said step (b), and wherein said step (b) comprises generating a plurality of projections of the characterizing ERP signal vector of the patient under assessment.

4. The method of claim 3, wherein said step (d) comprises the steps of:
   (i) for each ERP trial, concatenating the signals received by electrodes of an ERP trial apparatus in a predetermined order to form a concatenated signal;
   (ii) for each ERP trial, sampling the concatenated signal at a predetermined sampling rate, to form a vector of amplitude values for each ERP trial; and
   (iii) averaging corresponding amplitude values taken from each vector, to form a characterizing ERP signal vector of the patient under assessment.

5. The method of claim 4, wherein said step ii) comprises sampling each concatenated signal approximately once every 10 milliseconds.

6. The method of claim 3, wherein said step (b) comprises randomly deleting components of the characterizing ERP signal vector of the patient under assessment to create the projections.

7. The method of claim 3, wherein said step (b) comprises deleting components of the characterizing ERP signal vector of the patient under assessment according to a deterministic algorithm to create the projections.

8. The method of claim 1, wherein said step (c) comprises the step of:
   (i) comparing each projection with characterizing ERP signal vectors from other patients, to produce comparison results for each projection.

9. The method of claim 8, wherein said step (i) comprises comparing each projection with at least one characterizing ERP signal vector from at least one patient, respectively, known not to be afflicted with the neurological disorder.

10. The method of claim 8, wherein said step (i) comprises comparing each projection with at least one characterizing ERP signal vector from at least one patient, respectively, known to be afflicted with the neurological disorder.

11. The method of claim 1, wherein said step (c) comprises the steps of:
   (i) deriving a healthy weight value for each projection and each characterizing ERP signal vector from a healthy patient, wherein the healthy weight value is determined by a degree of correlation between the projection and the characterizing ERP signal vector from the healthy patient, such that a greater degree of correlation between the projection and the characterizing ERP signal vector from the healthy patient corresponds to a larger healthy weight value;
   (ii) deriving a disorder weight value for each projection and each characterizing ERP signal vector from a patient known to have the neurological disorder, wherein the disorder weight value is determined by a degree of correlation between the projection and the characterizing ERP signal vector from the patient known to have the neurological disorder, such that a greater degree of correlation between the projection and the characterizing ERP signal vector from the patient known to have the neurological disorder corresponds to a larger disorder weight value;
   (iii) for each characterizing ERP signal vector from a healthy patient, summing the healthy weight values for all projections, to produce a healthy sum corresponding to the associated healthy patient;
   (iv) for each characterizing ERP signal vector from a patient known to have the neurological disorder, summing the disorder weight values for all projections, to create a disorder sum corresponding to the associated patient known to have the neurological disorder;
   (v) comparing the healthy sums and the disorder sums; and
   (vi) deciding on the probable presence of the neurological disorder based on whether any of the disorder sums is greater than any of the healthy sums.

12. A computer program product comprising a computer usable medium having computer readable program code means embodied in the medium for causing an application program to execute on a computer that facilitates the diagnosis of a neurological disorder, the computer readable program code means comprising:
   (a) first computer readable program code means for causing the computer to characterize evoked response potential (ERP) signals obtained from a plurality of ERP trials conducted on a patient under assessment, to produce a characterizing ERP signal vector of the patient under assessment;
   (b) second computer readable program code means for causing the computer to generate a plurality of projections of the characterizing ERP signal vector of the patient under assessment;
   (c) third computer readable program code means for causing the computer to compare each projection with characterizing ERP signal vectors from other patients; and
   (d) fourth computer readable program code means for causing the computer to determine the probable presence of the neurological disorder by a weighted vote process that is based on comparison results of each projection.

13. A method of determining treatability, with respect to a first treatment regimen, of a patient under assessment, the method comprising the steps of:
   (a) performing a plurality of evoked response potential (ERP) trials on the patient under assessment;
   (b) generating a plurality of projections of ERP data, wherein the ERP data is derived from the plurality of ERP trials performed on the patient under assessment; and
   (c) assessing the likely responsiveness of the patient under assessment to the first treatment regimen, as indicated by the projections.

14. The method of claim 13, wherein said step (a) comprises the step of repeating an ERP trial approximately once every one to two seconds, for approximately 2 minutes.

15. The method of claim 13, further comprising the step of:
   (d) characterizing ERP signals obtained from the plurality of trials performed on the patient under assessment, to produce a characterizing ERP signal vector of the patient under assessment;
wherein said step (d) is performed after said step (a) and before said step (b), and wherein said step (b) comprises generating a plurality of projections of the characterizing ERP signal vector of the patient under assessment.

16. The method of claim 15 wherein said step (d) comprises the steps of:
   (i) for each ERP trial performed on the patient under assessment, concatenating the signal received by electrodes of an ERP trial apparatus in a predetermined order, to form a concatenated signal;
   (ii) for each ERP trial performed on the patient under assessment, sampling the concatenated signal at a predetermined sampling rate, to form a vector of amplitude values for each ERP trial; and
   (iii) averaging corresponding amplitude values taken from each vector, to form a characterizing ERP signal vector of the patient under assessment.

17. The method of claim 16, wherein said step (ii) comprises sampling each concatenated signal approximately once every ten milliseconds.

18. The method of claim 15, wherein said step (b) comprises randomly deleting components of the characterizing ERP signal vector of the patient under assessment to create the projections.

19. The method of claim 15, wherein said step (b) comprises deleting components of the characterizing ERP signal vector of the patient under assessment according to a deterministic algorithm to create the projections.

20. The method of claim 13, wherein said step (c) comprises the step of:
   (i) comparing each projection with at least one characterizing ERP signal vector from at least one patient, respectively, known to be treatable by the first treatment regimen.

21. The method of claim 13, wherein said step (c) comprises the steps of:
   (i) for each projection and each of at least one characterizing ERP signal vector from each of at least one patient, respectively, known to be treatable by the first treatment regimen, deriving a first weight value that is determined by a degree of correlation between the projection and the characterizing ERP signal vector from the patient known to be treatable by the first treatment regimen;
   (ii) for each characterizing ERP signal vector from a patient known to be treatable by the first treatment regimen, summing the first weight values for all projections to produce a first sum; and
   (iii) deciding on the probable responsiveness of the patient under assessment to the first treatment regimen, based on the first sums.

22. The method of claim 21, wherein said step (c) further comprises the steps of:
   (iv) for each projection and each of at least one characterizing ERP signal vector from at least one patient, respectively, known to be treatable by a second treatment regimen, deriving a second weight value for each projection, wherein the second weight value is determined by a degree of correlation between the projection and the characterizing ERP signal vector from the patient known to be treatable by the second treatment regimen;
   (v) for each characterizing ERP signal vector from a patient known to be treatable by the second treatment regimen, summing the second weight values for all projections, to produce a second sum;
   (vi) comparing the first sums and the second sums; and
   (vii) deciding on the likely responsiveness of the patient under assessment to the first treatment regimen, relative to the likely responsiveness to the second treatment regimen, based on the first and second sums.

23. A computer program product comprising a computer usable medium having computer readable program code means embodied in the medium for causing an application program to execute on a computer that facilitates the assessment of the likely responsiveness of a patient under assessment to a treatment regimen, the computer readable program code means comprising:
   (a) first computer readable program code means for causing the computer to characterize evoked response potential (ERP) signals obtained from a plurality of ERP trials, to produce a characterizing ERP signal vector of the patient under assessment;
   (b) second computer readable program code means for causing the computer to generate a plurality of projections of the characterizing ERP signal vector of the patient under assessment;

(c) third computer readable program code means for causing the computer to compare each projection with characterizing ERP signal vectors from other patients; and (d) fourth computer readable program code means for causing the computer to determine the probable treatability of the patient having a neurological disorder with respect to the treatment regimen, where the determination is based on comparison results of each projection.

24. A method of monitoring the response, to a treatment regimen, of a patient being treated for a neurological disorder, the method comprising the steps of:

(a) performing a plurality of evoked response potential (ERP) trials on the patient being treated;

(b) generating a plurality of projections of ERP data, wherein the ERP data is derived from the plurality of ERP trials performed on the patient being treated; and (c) assessing the current condition of the patient being treated, as indicated by the projections, after beginning the treatment regimen.

25. The method of claim 24 wherein said step (a) comprises the step of repeating an ERP trial approximately once every one to two seconds, for approximately two minutes.

26. The method of claim 24, further comprising the step of:

(d) characterizing ERP signals obtained from the plurality of trials performed on the patient being treated, to produce a characterizing ERP signal vector of the patient being treated;

wherein said step (d) is performed after said step (a) and before said step (b), and wherein said step (b) comprises generating a plurality of projections of the characterizing ERP signal vector of the patient being treated.

27. The method of claim 26, wherein said step (d) comprises the steps of:

(i) for each ERP trial, concatenating the signals received by electrodes of an ERP trial apparatus in a predetermined order to form a concatenated signal;

(ii) for each ERP trial, sampling the concatenating signal at a predetermined sampling rate, to form a vector of amplitude values for each ERP trial; and (iii) averaging corresponding amplitude values taken from each vector, to form a characterizing ERP signal vector of the patient being treated.

28. The method of claim 27 wherein said step (ii) comprises sampling each concatenated signal approximately once every ten milliseconds.

29. The method of claim 26, wherein said step (b) comprises randomly deleting components of the characterizing ERP signal vector of the patient being treated, to create the projections.

30. The method of claim 26, wherein said step (b) comprises deleting components of the characterizing ERP signal vector of the patient being treated, wherein deletions are performed according to a deterministic algorithm to create the projections.

31. The method of claim 24, wherein said step (c) comprises the step of:

(i) comparing each projection with at least one characterizing ERP signal vector from at least one patient, respectively, wherein each such patient has a known neurological condition.

32. The method of claim 31, wherein said step (i) comprises the steps of:

(A) for each of at least one characterizing ERP signal vector from at least one patient, respectively, and for each projection, deriving a progress weight value, wherein the progress weight value is determined by a degree of correlation between the projection and the characterizing ERP signal vector from a patient having a known neurological condition;

(B) for each of at least one characterizing ERP signal vector from at least one patient, respectively, summing the progress weight values for all projections, to produce a progress sum; and (C) deciding on the probable current condition of the patient being treated, based on the progress sums.

33. The method of claim 31, wherein step (i) comprises the step of comparing each projection with at least one characterizing ERP signal vector from at least one patient, respectively, wherein at least one such patient comprises a patient who is neurologically healthy.

34. The method of claim 31, wherein step (i) comprises the step of comparing each projection with at least one characterizing ERP signal vector from at least one patient, respectively, wherein at least one such patient comprises a patient who is afflicted with the neurological disorder of the patient being treated.

35. A computer program product comprising a computer usable medium having computer readable code means embodied in the medium for causing an application program to execute on a computer that facilitates the assessment of a current condition of a patient being treated for a neurological disorder after beginning a treatment regimen, the computer readable code means comprising:

(a) first computer readable program code means for causing the computer to characterize evoked response potential (ERP) signals obtained from a plurality of ERP trials performed on the patient being treated, to produce a characterizing ERP signal vector of the patient being treated;

(b) second computer readable program code means for causing the computer to generate a plurality of projections of the characterizing ERP signal vector of the patient being treated;

(c) third computer readable program code means for causing the computer to compare each projection with characterizing ERP signal vectors from other patients; and (d) fourth computer readable code means for causing the computer to determine the probable current condition of the patient being treated, where the determination is based on comparison results of each projection.

36. A method of assessing a patient with respect to the nature and extent of side effects experienced in response to a treatment regimen, wherein the patient is being treated for a neurological disorder, the method comprising the steps of:

(a) performing a plurality of evoked response potential (ERP) trials on the patient under assessment;

(b) generating a plurality of projections of ERP data, wherein the ERP data is derived from the plurality of ERP trials performed on the patient under assessment; and (c) assessing the nature and extent of the side affects as indicated by the projections.

37. The method of claim 36 wherein said step (a) comprises the step of repeating an ERP trial approximately once every one to two seconds, for approximately two minutes.

38. The method of claim 36, further comprising the step of:
  (d) characterizing ERP signals obtained from the plurality of trials performed on the patient under assessment, to produce a characterizing ERP signal vector of the patient under assessment;
wherein said step (d) is performed after said step (a) and before said step (b), and wherein said step (b) comprises generating a plurality of projections of the characterizing ERP signal vector of the patient under assessment.

39. The method of claim 38, wherein said step (d) comprises the steps of:
  (i) for each ERP trial, concatenating the signals received by electrodes of an ERP trial apparatus in a predetermined order to form a concatenated signal;
  (ii) for each ERP trial, sampling the concatenated signal at a predetermined sampling rate, to form a vector of amplitude values for each ERP trial; and
  (iii) averaging corresponding amplitude values taken from each vector, to form a characterizing ERP signal vector of the patient under assessment.

40. The method of claim 39, wherein said step (ii) comprises sampling each concatenated signal approximately once every ten milliseconds.

41. The method of claim 38, wherein said step (b) comprises randomly deleting components of the characterizing ERP signal vector of the patient under assessment to create the projections.

42. The method of claim 38, wherein said step (b) comprises deleting components of the characterizing ERP signal vector of the patient under assessment according to a deterministic algorithm to create the projections.

43. The method of claim 36, wherein step (c) comprises the step of:
  (i) comparing each projection with at least one characterizing ERP signal vector from at least one patient, respectively, wherein the at least one patient has at least one known neurological condition, respectively.

44. The method of claim 43, wherein step (i) comprises the steps of:
  (A) for each characterizing ERP signal vector from a patient having a known neurological condition and for each projection, deriving a side effect weight value, wherein each side effect weight value is determined by a degree of correlation between the projection and the characterizing ERP signal vector of the patient having a known neurological condition;
  (B) for each characterizing ERP signal vector from a patient having a known neurological condition, summing the side affect weight values for all projections to produce a side effect sum; and
  (C) deciding on the probable nature and extent of the side effects, based on the side effect sums.

45. A computer program product comprising a computer usable medium having computer readable program code means embodied in the medium for causing an application program to execute on a computer that facilitates the assessment of the nature and extent of side affects resulting from a treatment regimen, the computer readable program code means comprising:
  (a) first computer readable program code means for causing the computer to characterize evoked response potential (ERP) signals obtained from a plurality of ERP trials performed on a patient under assessment, to produce a characterizing ERP signal vector of the patient under assessment;
  (b) second computer readable program code means for causing the computer to generate a plurality of projections of the characterizing ERP signal vector of the patient under assessment;
  (c) third computer readable program code means for causing the computer to compare each projection with characterizing ERP signal vectors from other patients; and
  (d) fourth computer readable code means for causing the computer to determine the probable nature and extent of side affects resulting from the treatment regimen, wherein the determination is based on comparison results of each projection.

46. A method of assessing the results of a treatment regimen for a neurological disorder, comprising the steps of:
  (a) performing a plurality of evoked response potential (ERP) trials on a test patient afflicted with the neurological disorder and treated with the test regimen;
  (b) generating a plurality of projections of ERP data, wherein the ERP data is derived from the plurality of ERP trials performed on the test patient; and
  (c) determining the neurological condition of the test patient as indicated by the projections.

47. The method of claim 46 wherein said step (a) comprises the step of repeating an ERP trial approximately once every one to two seconds, for approximately two minutes.

48. The method of claim 46, further comprising the step of:
  (d) characterizing ERP signals obtained from the plurality of trials performed on the test patient, to produce a characterizing ERP signal vector of the test patient;
wherein said step (d) is performed after said step (a) and before said step (b), and wherein said step (b) comprises generating a plurality of projections of the characterizing ERP signal vector of the test patient.

49. The method of claim 48, wherein said step (d) comprises the steps of:
  (i) for each ERP trial, concatenating the signals received by electrodes of an ERP trial apparatus in a predetermined order to form a concatenated signal;
  (ii) for each ERP trial, sampling the concatenated signal at a predetermined sampling rate, to form a vector of amplitude values for each ERP trial; and
  (iii) averaging corresponding amplitude values taken from each vector, to form a characterizing ERP signal vector of the test patient.

50. The method of claim 49, wherein said step (ii) comprises sampling each concatenated signal approximately once every ten milliseconds.

51. The method of claim 48, wherein said step (b) comprises randomly deleting components of the characterizing ERP signal vector of the test patient to create the projections.

52. The method of claim 48, wherein said step (b) comprises deleting components of the characterizing ERP signal vector of the test patient according to a deterministic algorithm to create the projections.

53. The method of claim 46, wherein step (c) comprises the step of:
  (i) comparing each projection with at least one characterizing ERP signal vector from at least one patient, respectively, wherein the at least one patient has at least one known neurological condition, respectively.

54. The method of claim 53, wherein step (i) comprises the steps of:

(A) for each characterizing ERP signal vector from a patient having a known neurological condition, and for each projection, deriving a comparison weight value, wherein each comparison weight value is determined by a degree of correlation between the projection and the characterizing ERP signal vector of the patient having a known neurological condition;

(B) for each characterizing ERP signal vector from a patient having a known neurological condition, summing the comparison weight values for all projections to produce a comparison sum; and (C) characterizing the effects of the treatment regimen, based on the comparison sums.

55. A computer program product comprising a computer usable medium having computer readable program code means embodied in the medium for causing an application program to execute on a computer that facilitates the assessment of the results of a treatment regimen for a neurological disorder, the computer readable program code means comprising:

(a) first computer readable program code means for causing the computer to characterize evoked response potential (ERP) signals obtained from a plurality of ERP trials performed on a test patient to produce a characterizing ERP signal vector of the test patient;

(b) second computer readable program code means for causing the computer to generate a plurality of projections of the characterizing ERP signal vector of the test patient;

(c) third computer readable program code means for causing the computer to compare each projection with characterizing ERP signal vectors from other patients; and (d) fourth computer readable code means for causing the computer to determine the probable neurological condition of the test patient result from the treatment regimen, wherein the determination is based on comparison results of each projection.

* * * * *

UNITED STATES PATENT AND TRADEMARK OFFICE
CERTIFICATE OF CORRECTION

PATENT NO. : 6,223,074 B1
DATED : April 24, 2001
INVENTOR(S) : Granger

It is certified that error appears in the above-identified patent and that said Letters Patent is hereby corrected as shown below:

Column 1,
Lines 15-16, please replace "Part of the work performed during development of this invention utilized U.S. Government funds." with -- This invention was made with Government support under N00014-97-C-0192 awarded by the Office of Naval Research. --.

Signed and Sealed this

Twenty-first Day of January, 2003

JAMES E. ROGAN
*Director of the United States Patent and Trademark Office*